(12) United States Patent
Himmler et al.

(10) Patent No.: US 10,246,407 B2
(45) Date of Patent: Apr. 2, 2019

(54) PROCESS FOR PREPARING BIPHENYLAMINES FROM ANILIDES BY RUTHENIUM CATALYSIS

(71) Applicant: BAYER CROPSCIENCE AKTIENGESELLSCHAFT, Duesseldorf (DE)

(72) Inventors: Thomas Himmler, Odenthal (DE); Lars Rodefeld, Leverkusen (DE); Jonathan Hubrich, Goettingen (DE); Lutz Ackermann, Goettingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/305,865

(22) PCT Filed: Apr. 22, 2015

(86) PCT No.: PCT/EP2015/058636
§ 371 (c)(1),
(2) Date: Oct. 21, 2016

(87) PCT Pub. No.: WO2015/162144
PCT Pub. Date: Oct. 29, 2015

(65) Prior Publication Data
US 2017/0044094 A1    Feb. 16, 2017

(30) Foreign Application Priority Data

Apr. 25, 2014 (EP) .................. 14166058
Oct. 16, 2014 (EP) .................. 14189192

(51) Int. Cl.
*C07C 231/12* (2006.01)
(52) U.S. Cl.
CPC .................. *C07C 231/12* (2013.01)
(58) Field of Classification Search
None
See application file for complete search history.

(56) References Cited

U.S. PATENT DOCUMENTS

| | | | |
|---|---|---|---|
| 8,455,689 B2 | 6/2013 | Dockner et al. | |
| 2006/0116414 A1 | 6/2006 | Dunkel et al. | |
| 2008/0015244 A1 | 1/2008 | Dunkel et al. | |
| 2008/0194835 A1* | 8/2008 | Jorges | C07C 209/62 548/374.1 |
| 2010/0185015 A1 | 7/2010 | Straub et al. | |

(Continued)

FOREIGN PATENT DOCUMENTS

| EP | 2119697 A1 | 11/2009 |
|---|---|---|
| WO | 01/42223 A1 | 6/2001 |

(Continued)

OTHER PUBLICATIONS

Chinnagolla ("Ruthenium-catalyzed ortho-arylation of acetanilides with aromatic boronic acids: an easy route to prepare phenanthridines and carbazoles" Chem. Commun. 2014, 50, 2442-2444, first publicly available on Jan. 7, 2014, and including SI, p. 1-59).*

(Continued)

*Primary Examiner* — Amy C Bonaparte
(74) *Attorney, Agent, or Firm* — McBee Moore Woodward & Vanik IP, LLC

(57) ABSTRACT

The present invention relates to a novel process for preparing substituted biphenylamides of the general formula (V)

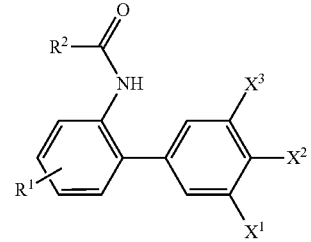

characterized in that
anilides of the formula (II)

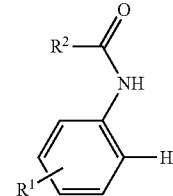

in a solvent other than tetrahydrofuran,
are reacted with an organoboron compound of the formula (III)

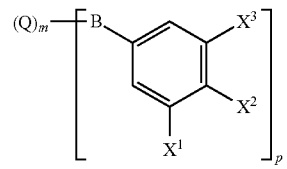

in the presence of a catalyst system consisting of a ruthenium catalyst, an activator, an oxidizing agent and a metal triflate.

20 Claims, No Drawings

(56) References Cited

U.S. PATENT DOCUMENTS

| | | |
|---|---|---|
| 2011/0092736 A1 | 4/2011 | Dockner |
| 2015/0203440 A1 | 7/2015 | Riedrich et al. |

FOREIGN PATENT DOCUMENTS

| | | |
|---|---|---|
| WO | 03/070705 A1 | 8/2003 |
| WO | 2007/138089 A1 | 12/2007 |
| WO | 2009/003650 A1 | 1/2009 |
| WO | 2009/135598 A1 | 11/2009 |
| WO | 2014/019995 A1 | 2/2014 |

OTHER PUBLICATIONS

Jeganmohan ("Regioselective ortho-arylation and alkenylation of N-alkyl benzamides with boronic acids via ruthenium-catalyzed C—H bond activation: an easy route to fluorenones synthesis" Org. Lett., 2012, p. 5246-5249).*

Brasche et al. "Twofold C—H Functionalization: Palladium-Catalyzed Ortho Arylation of Anilides", Organic Letters, (2008) vol. 10, No. 11, pp. 2207-2210.

Wencel-Delord et al. "[RhIIICp*]-Catalyzed Dehydrogenative ArylAryl Bond Formation", Angew. Chem. Inst. Ed. (2012) vol. 51, pp. 2247-2251.

Jeong et al. "A Facile Preparation of the Fluoroaryl Zinc Halides: an Application to the Synthesis of Diflunisal", Bull. Korean Chem. Soc. (2000), vol. 21, No. 2, pp. 165-166.

Fuerstner et al. "What is Amphidinolide V? Report on a Likely Conquest", Chem, Int. Ed. vol. 46 (2007), pp. 5554-5558.

Nishikata et al "Cationic Palladium(II) Catalysis: C—H Activation/Suzuki-Miyaura Couplings at Room Temperature", J. Amer. Chem. Soc., vol. 132 (2010), pp. 4978-4979.

* cited by examiner

PROCESS FOR PREPARING BIPHENYLAMINES FROM ANILIDES BY RUTHENIUM CATALYSIS

CROSS REFERENCE TO RELATED APPLICATIONS

This application is a § 371 National State Application of PCT/EP2015/058636, filed Apr. 22, 2015, which claims priority to European Application Nos. 14166058.9 filed Apr. 25, 2014 and 14189192.9 filed Oct. 16, 2014.

BACKGROUND OF THE INVENTION

Field of the Invention

The present invention relates to a novel process for preparing substituted biphenylamides and, in a further optional stage, biphenylamines.

Description of Related Art

Biaryl compounds, especially biphenyl compounds, are of industrial significance as fine chemicals, intermediates for pharmaceuticals, optical brighteners and agrochemicals.

A method possible in principle for preparation of biaryl compounds in transition metal-catalysed cross-coupling is that of double C—H activation (see, for example, S. L. Buchwald et al, Org. Lett. 2008, 10(11), 2207-10; F. Glorius et al., Angew. Chem. Int. Ed. 2012, 51, 2247-51; WO 2014/019995). Although these methods dispense with the synthesis of a boronic acid, for example, as a starting compound, they have serious disadvantages. For instance, costly palladium or rhodium complexes are typically used as catalysts. Moreover, the generally low reactivity of C—H bonds frequently leads to selectivity problems (functionalization of one C—H bond in the presence of other C—H bonds). In addition, there is competition between hetero- and homo-coupling.

Moreover, it is already known that biphenyl derivatives can be prepared from phenylboronic acids and phenyl halides by a Suzuki or Stille coupling, i.e. by a palladium-catalysed reaction (cf., for example, WO 01/42223, WO 03/070705, WO 07/138089, WO 09/003650, WO 09/135598).

It is additionally known that biphenyl derivatives are obtained by reacting arylzinc halides with aryl halides (Bull. Korean Chem. Soc. 2000, 21, 165-166).

A disadvantage of these processes is the high production costs. Transition metal-catalysed cross-couplings (for example according to Suzuki) require relatively large amounts of costly palladium catalysts or else (Bull. Korean Chem. Soc. 2000, 21, 165-166) the use of virtually equivalent amounts of zinc which have to be disposed of as waste. Moreover, activation of the zinc requires carcinogenic dibromomethane.

It is additionally known that biphenyl derivatives are obtained by reacting acetanilides with aromatic boronic acids in the presence of palladium catalysts, copper(II) triflate (Cu(OTf)$_2$) and silver oxide (Ag$_2$O) (Z. Shi et al., Angew. Chem. Int. Ed. 46 (2007) 5554-8). Here too, the high costs of the palladium catalyst are disadvantageous.

It is likewise known that biphenyl derivatives are obtained by reacting arylurea compounds with aromatic boronic acids in the presence of palladium catalysts and benzoquinone (B. H. Lipshutz et al., J. Amer. Chem. Soc. 132 (2010) 4978-9). Again, the high costs of the palladium catalyst are disadvantageous.

It is additionally known that biphenyl derivatives are obtained by reacting acetanilides with aromatic boronic acids in the presence of ruthenium(II) complexes, silver hexafluoroantimonate (AgSbF$_6$), Cu(OTf)$_2$ and Ag$_2$O (R. K Chinnagolla and M. Jeganmohan, Chemical Communication, January 2014, accepted for publication).

However, the authors state that the only suitable solvent is tetrahydrofuran, while other solvents preferred in industry that are mentioned, for example methanol, toluene or dimethylformamide, are described as entirely ineffective, i.e. without conversion for the purposes of the disclosure, and so the reaction cannot be carried out by the person skilled in the art and hence is not disclosed either.

SUMMARY

The problem addressed by the present invention was thus that of providing a novel process through which biphenylamines can be obtained with a high overall yield and high purity without the use of costly palladium catalysts and under the industrially preferred reaction conditions, especially with industrially preferred solvents.

The present invention accordingly provides a process for preparing biphenylamides of the general formula (V) and subsequently, in an optional second stage, biphenylamines of the general formula (I)

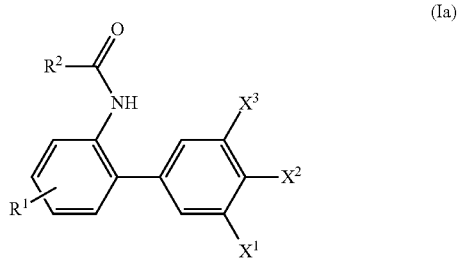
(Ia)

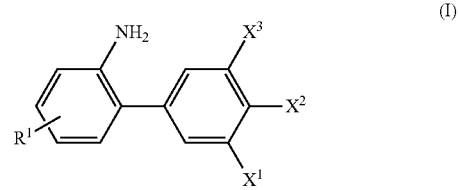
(I)

in which $R^1$ is hydrogen, hydroxyl, fluorine, chlorine, $C_1$-$C_4$-alkyl, $C_1$-$C_4$-alkoxy, $C_1$-$C_4$-alkylthio or $C_1$-$C_4$-haloalkyl, $R^2$ is $C_1$-$C_4$-alkyl, $C_6$-$C_{10}$-aryl or $C_6$-$C_{10}$-aryl-$CH_2$—, and $X^1$ is hydrogen, $C_1$-$C_4$-alkyl, $C_1$-$C_4$-alkoxy, fluorine or chlorine, $X^2$ is hydrogen, $C_1$-$C_4$-alkyl, $C_1$-$C_4$-alkoxy, fluorine or chlorine, $X^3$ is hydrogen, $C_1$-$C_4$-alkyl, $C_1$-$C_4$-alkoxy, fluorine or chlorine,
characterized in that
(1) in a first step
anilides of the formula (II)

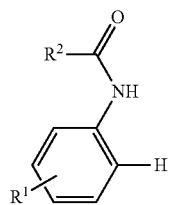

(II)

in which
$R^1$ and $R^2$ are each as defined above,
in a solvent other than tetrahydrofuran (THF),
are reacted with an organoboron compound of the formula (III)

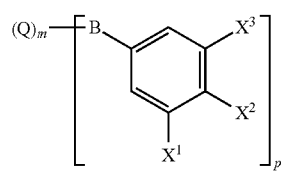

(III)

in which
$X^1$, $X^2$ and $X^3$ are each as defined above,
and which is selected from one of the following groups consisting of:
(I) boronic acids of the formula (III) in which
  Q is a hydroxyl group,
  m is 2,
  p is 1,
  or the anhydrides, dimers or trimers of these boronic acids;
(II) boronic acid derivatives of the formula (III) in which
  Q is F, Cl, Br, I, $C_1$-$C_4$-alkyl, $C_6$-$C_{10}$-aryl, $C_1$-$C_4$-alkoxy or $C_6$-$C_{10}$-aryloxy,
  m is 2,
  p is 1;
(III) borinic acids of the formula (III) in which
  Q is OH, F, Cl, Br, I, $C_1$-$C_4$-alkyl, $C_6$-$C_{10}$-aryl, $C_1$-$C_4$-alkoxy or $C_6$-$C_{10}$-aryloxy,
  m is 1,
  p is 2;
(IV) cyclic boronic esters of the formula (III) in which
  Q is a $C_2$-$C_3$-alkyldioxy radical which, together with the boron atom to which it is bonded, forms a 5- or 6-membered ring optionally substituted by one or more $C_1$-$C_4$-alkyl radicals,
  m is 2,
  p is 1;
(V) boronates of the formula (III) in which
  Q is OH, F, Cl, Br, I, $C_1$-$C_4$-alkyl, $C_6$-$C_{10}$-aryl, $C_1$-$C_4$-alkoxy or $C_6$-$C_{10}$-aryloxy,
  m is 3,
  p is 1
  and the negative charge of the boronate anion is compensated for by a cation, preferably by a metal cation, the metal further preferably being selected from metals of main groups 1 and 2 and aluminium, iron and copper,
(VI) triarylboranes of the formula (III) in which
  m is 0,
  p is 3;
(VII) tetraarylborates of the formula (IV) in which
  m is 0,
  p is 4,
  and the negative charge of the tetraarylborate anion is compensated for by a cation, preferably by a metal cation, the metal further preferably being selected from metals of main groups 1 and 2 and aluminium, iron and copper,
in the presence of a catalyst system consisting of a ruthenium catalyst, an activator, an oxidizing agent and a metal triflate, where the metal is preferably selected from the group comprising Li, Na, K, Mg, Ca, Mn, Fe, Co, Ni, Cu and Zn, further preferably from the group comprising Fe and Ni, and more preferably Fe.

DETAILED DESCRIPTION OF A PREFERRED EMBODIMENT

Preferably, Cu and Fe are each in their highest oxidation states, while all other metals except for the alkali metals are preferably in the +II oxidation state.
In an optional second stage, the anilides of the formula (V) thus obtained

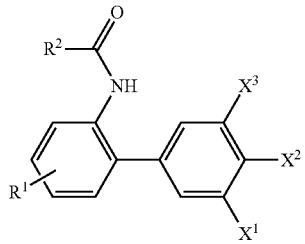

(V)

in which $R^1$, $R^2 X^1$, $X^2$ and $X^3$ are each as defined above, are acid- or base-hydrolysed (removal of the [—C(=O)$R^2$] protecting group on the nitrogen) by known organic chemistry methods.
Preferably, the protecting group on the nitrogen is removed in the second stage.
In a preferred embodiment, boronic acids are used as the component of the formula (III), and more preferably Q=OH, m=2 and p=1.
$C_1$-$C_4$-Alkyl encompasses methyl, ethyl, propyl and isopropyl, butyl, isobutyl and tert-butyl and is more preferably methyl.
$C_1$-$C_4$-Alkoxy encompasses methoxy, ethoxy, propoxy, isopropoxy and butoxy and is more preferably methoxy.
In an alternative embodiment, the catalyst system consists of a ruthenium catalyst, an activator, an oxidizing agent and a metal sulphate, where the metal is preferably selected from the group comprising Mn(II), Fe(III), Co(II), Ni(II), Cu(II), Zn(II) Mg(II), Ca(II) and Al(III), further preferably from the group comprising Fe(II) and Cu(II), and more preferably Cu(II).
The advantage of this embodiment is that the much less expensive sulphates, which are thus of greater economic interest, can be used with only a slightly reduced yield compared to the triflates.

In a further alternative embodiment, the activator of the catalyst system is selected from the group comprising Cu(I) oxide and Cu(II) oxide.

While the alternative embodiments differ in the abovementioned type of metal salt, the specifications of the present description additionally apply to the other reaction parameters and co-reactants. Excluded from this is the fact that THF can also be used as solvent with good yields in reactions without metal triflate.

It is surprisingly possible through this reaction sequence to prepare the biphenylamines of the formula (I) in good yields without the use of halogenated anilides, without use of costly palladium catalysts and under industrially advantageous reaction conditions, especially in terms of the solvents used, which do not have a tendency to form peroxides, unlike tetrahydrofurans.

If N-(4-fluorophenyl)acetamide and phenylboronic acid are used as starting materials, the process according to the invention can be illustrated by way of example by the following formula scheme:

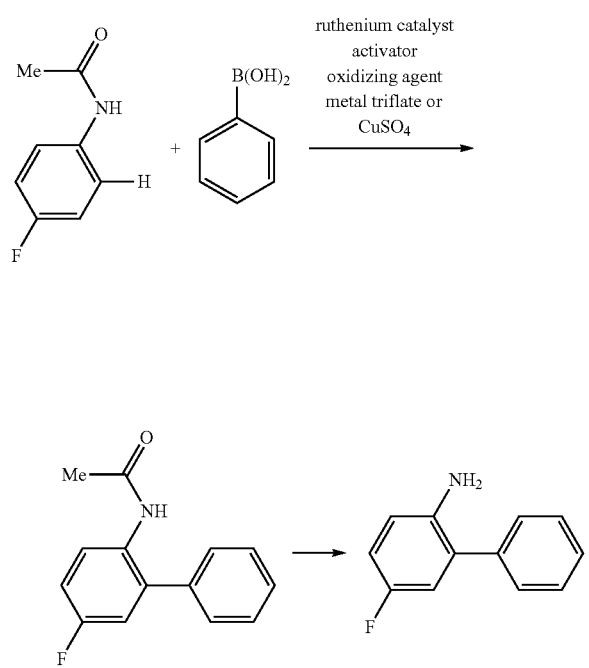

If N-(4-fluorophenyl)acetamide and phenylborinic acid, for example, are used as starting materials, the process according to the invention can be illustrated by way of example by the following formula scheme:

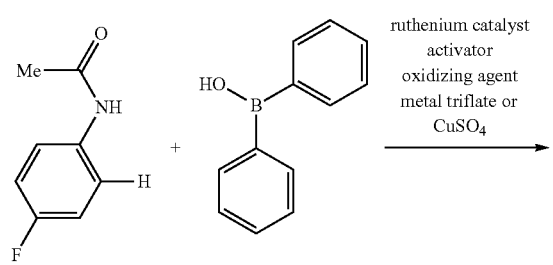

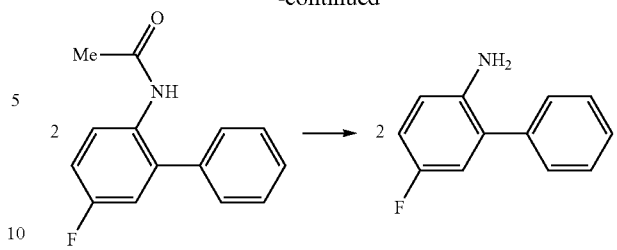

The organoboron compounds of the formula (III) are known in principle and can be prepared by known methods.

Preference is given to the performance of the process according to the invention using starting materials in which the radicals specified are each defined as follows. The preferred, particularly preferred and very particularly preferred definitions apply to all the compounds in which the respective radicals occur:

$R^1$ is preferably hydrogen, fluorine and chlorine.

$R^2$ is further preferably fluorine or chlorine, where the substituent is preferably in the 3, 4 or 5 position, further preferably in the 4 or 5 position and more preferably in the 5 position [cf., for example, formula (I)].

$R^1$ is more preferably fluorine in the abovementioned positions, most preferably in the 4 position.

In an alternative embodiment, $R^1$ is preferably trifluoromethyl, where trifluoromethyl is preferably in the 4 or 5 position, further preferably in the 5 position, of the respective compound.

In a further alternative embodiment, $R^1$ is preferably methoxy or methylthio, preferably in the 4, 5 or 6 position, further preferably in the 5 position, of the respective compound.

$R^2$ is preferably methyl, ethyl, isopropyl, tert-butyl, phenyl or benzyl.

$R^2$ is further preferably methyl, phenyl or benzyl.

$R^2$ is more preferably methyl.

$X^1$ is preferably hydrogen, methyl, fluorine or chlorine.

$X^1$ is further preferably fluorine or chlorine.

$X^1$ is more preferably chlorine.

$X^2$ is preferably hydrogen, methyl, fluorine or chlorine.

$X^2$ is further preferably fluorine or chlorine.

$X^2$ is more preferably chlorine.

$X^3$ is preferably hydrogen, methyl, fluorine or chlorine.

$X^3$ is further preferably fluorine or chlorine.

$X^3$ is more preferably chlorine.

In a particularly preferred embodiment, one of the $X^1$, $X^2$ and $X^3$ substituents is hydrogen, but it is particularly preferable that adjacent substituents are not both hydrogen.

Preferred embodiments of compounds of the formula (V) in the context of the present invention are (the numbers for $R^1$ each indicate the position):

|  | $R^1$ | $R^2$ | $X^1$ | 2 | $X^3$ |
|---|---|---|---|---|---|
| V1 | h | Me | Cl | Cl | h |
| V2 | H | MU | H | Cl | H |
| V3 | 4 | Me | Cl | Cl | H |
| V4 | F (3) | Me | Cl | Cl | h |
| V5 | 5 | Me | Cl | Cl | H |
| V6 | Cl (4) | Me | Cl | Cl | H |
| V7 | Cl (3) | Me | Cl | Cl | H |
| V8 | Cl (5) | Me | Cl | Cl | H |
| V9 | Me (4) | Me | Cl | Cl | H |
| V10 | Me (5) | Me | Cl | Cl | H |
| V11 | F (4) | Me | Cl | Cl | Cl |

-continued

|  | R¹ | R² | X¹ | 2 | X³ |
|---|---|---|---|---|---|
| V12 | H | Me | H | H | H |
| V13 | H | Me | F | F | F |
| V14 | OH (5) | Me | H | H | H |
| V15 | Et (5) | Me | H | H | H |
| V16 | OMe (4) | Me | H | H | H |
| V17 | H | Me | H | OMe | H |
| V18 | H | Me | H | Me | H |
| V19 | H | iPr | H | H | H |
| V20 | H | tBu | H | H | H |

The anilides of the formula (II) for use as starting materials in the first stage in the performance of the process according to the invention are known or can be obtained by known methods.

The first stage of the process according to the invention is performed in the presence of a ruthenium catalyst. Ruthenium catalysts used are, for example, ruthenium complexes such as [{RuCl$_2$(p-cymene)}$_2$], [{RuCl$_2$(cumene)}$_2$], [{RuCl$_2$(benzene)}$_2$], [{RuCl$_2$(C$_6$Me$_6$)}$_2$], [Cp*Ru(PPh$_3$)$_2$Cl] (Cp*=pentamethylcyclopentadienyl). Preference is given to using [{RuCl$_2$(p-cymene)}$_2$].

The amount of ruthenium catalyst can be varied within wide limits. Typically, amounts of 0.1 to 20 mole percent of the corresponding complex are used. Preferably, 1 to 10 mole percent of the corresponding complex is used.

The first stage of the process according to the invention is performed in the presence of an activator which generates the actually active catalyst from the ruthenium complex used. Such activators used are typically AgSbF$_6$, KPF$_6$, NaPF$_6$, AgF, AgBF$_4$. Preference is given to using AgSbF$_6$, AgBF$_4$ and KPF$_6$, particular preference to using AgSbF$_6$.

The activator is used in amounts of 1 to 4 molar equivalents, based on the ruthenium complex. Preference is given to using 1.5 to 3 equivalents.

The first stage of the process according to the invention is performed in the presence of at least one oxidizing agent, the oxidizing agent used preferably being Ag$_2$O.

The oxidizing agent is used in amounts of 0.5 to 2 molar equivalents, based on the anilide of the formula (II). Preference is given to using 1 to 2 equivalents.

The first stage of the process according to the invention is performed in the presence of a metal triflate or in the presence of copper(II) sulphate or copper(I) or copper(II) oxide. Metal triflates used are compounds such as copper(II) triflate, manganese(II) triflate, cobalt(II) triflate, nickel(II) triflate, zinc(II) triflate, iron(II) triflate, iron(III) triflate, lithium triflate, sodium triflate, potassium triflate, magnesium triflate or calcium triflate, for example. Preference is given to using the compounds mentioned further up, especially sodium triflate, potassium triflate, manganese triflate, zinc triflate, nickel(II) triflate, iron(II) triflate and iron(III) triflate. Very particular preference is given to using iron triflates and nickel(II) triflate.

The metal triflate (or metal sulphate or copper(I) or copper(II) oxide) is used in amounts of 1 to 4 molar equivalents, based on the ruthenium complex. Preference is given to using 1.5 to 3 equivalents.

The first stage of the process according to the invention is performed in solvents or solvent mixtures selected from the group comprising N,N-dialkylalkanamides, for example N-methylpyrrolidone (NMP), dimethylformamide (DMF) and dimethylacetamide (DMA), dimethoxyethane (DME), methanol, ethyl acetate and water, and mixtures of these solvents.

Preferred solvents or solvent mixtures are those selected from the group comprising N,N-dialkylalkanamides, and further preferably among these N-methylpyrrolidone (NMP), dimethylformamide (DMF) and dimethylacetamide (DMA), and more preferably DMF, most preferably dried DMF (storage over 4 angstrom molecular sieve).

From an environmental point of view, water is a preferred solvent, which surprisingly gave the product in a relatively good yield.

For non-triflate-activated reactions in alternative embodiments, it is likewise possible to use THF as solvent with good yields.

The first stage of the process according to the invention is generally performed at temperatures in the range from 20° C. to 200° C., preferably in the range from 50° C. to 150° C.

In the performance of the first stage of the process according to the invention, generally an excess of organoboron compound of the formula (III) is used for 1 mol of anilide of the formula (II).

The second stage of the process according to the invention, i.e. the elimination of the [—C(=O)R²] protecting group on the nitrogen, can be effected under either basic or acidic conditions by known methods (cf., for example, T.W. Greene, P.G.M. Wuts, Protective Groups in Organic Synthesis, Ed. 3, New York, Wiley & Sons, 1999).

Both stages of the process according to the invention are, unless stated otherwise, generally conducted under standard pressure. However, it is also possible to work under elevated or reduced pressure.

In a preferred embodiment of the process according to the invention, the solvent is an N,N-dialkylalkanamide and the triflate is selected from the group comprising iron(III) triflate and nickel(II) triflate, more preferably iron(III) triflate. It is additionally preferable in this combination that the catalyst is [{RuCl$_2$(p-cymene)}$_2$]. Even further preferably, the activator is AgSbF$_6$ and the oxidizing agent is Ag$_2$O.

The biphenylamines of the formula (I) are valuable intermediates for preparation of active fungicidal ingredients (cf. WO 03/070705).

The process according to the invention is to be illustrated by the examples which follow, without being limited thereto.

PREPARATION EXAMPLES

Example 1

N-([1,1'-Biphenyl]-2-yl)acetamide

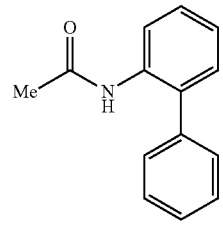 [SMILES: CC(=O)Nc1ccccc1-c1ccccc1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and phenylboronic acid (183 mg, 1.5 mmol) in dry DMF (3.0 ml)

was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 162 mg of N-([1,1'-biphenyl]-2-yl)acetamide were obtained as a colourless solid (77% of theory). M.p.=113-115° C. $^1$H NMR (CDCl$_3$, 300 MHz): δ=8.21 (d, J=8.2 Hz, 1H), 7.51-7.30 (m, 6H), 7.24-7.13 (m, 3H), 1.98 (s, 3H). $^{13}$C NMR (CDCl$_3$, 75 MHz): δ=168.2 (C$_q$), 138.1 (C$_q$), 134.6 (C$_q$), 132.2 (C$_q$), 130.0 (CH), 129.1 (CH), 129.0 (CH), 128.2 (CH), 127.9 (CH), 124.3 (CH), 121.7 (CH), 24.4 (CH$_3$). IR (neat): 3284, 3230, 3054, 3027, 1658, 1531, 1433, 1301, 755, 741, 703, 662, 520 cm$^{-1}$. MS (EI) m/z (relative intensity): 211 ([M$^+$] 34), 169 (100), 139 (7), 115 (5), 43 (15). HR-MS (ESI) m/z calculated for C$_{14}$H$_{13}$NO [M$^+$] 211.0997. found 211.0996.

Example 2: (Comp.)

N-([1,1'-Biphenyl]-2-yl)acetamide

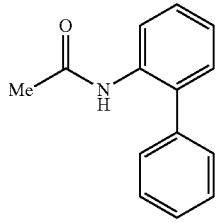 [SMILES: CC(=O)Nc1ccccc1-c1ccccc1]

The procedure was as described in Example 1, except that the reaction was conducted in THF rather than in DMF. 116 mg of N-([1,1'-biphenyl]-2-yl)acetamide were obtained as a colourless solid (55% of theory).

Example 2a

N-([1,1'-Biphenyl]-2-yl)acetamide

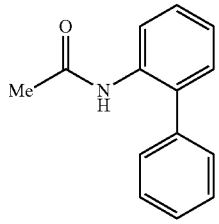 [SMILES: CC(=O)Nc1ccccc1-c1ccccc1]

The procedure was as described in Example 1, except that the reaction was conducted in ethyl acetate rather than in DMF. N-([1,1'-Biphenyl]-2-yl)acetamide was obtained as a colourless solid (55% of theory).

Example 2b

N-([1,1'-Biphenyl]-2-yl)acetamide

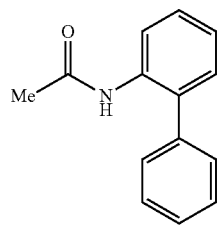 [SMILES: CC(=O)Nc1ccccc1-c1ccccc1]

The procedure was as described in Example 1, except that the reaction was conducted in methanol rather than in DMF. N-([1,1'-Biphenyl]-2-yl)acetamide was obtained as a colourless solid (70% of theory).

Example 2c

N-([1,1'-Biphenyl]-2-yl)acetamide

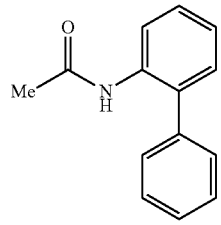 [SMILES: CC(=O)Nc1ccccc1-c1ccccc1]

The procedure was as described in Example 1, except that the reaction was conducted in dichloroethane rather than in DMF. N-([1,1'-Biphenyl]-2-yl)acetamide was obtained as a colourless solid (57% of theory).

Example 2d

N-([1,1'-Biphenyl]-2-yl)acetamide

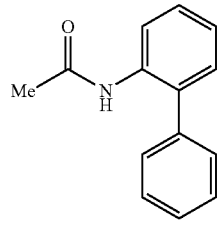 [SMILES: CC(=O)Nc1ccccc1-c1ccccc1]

The procedure was as described in Example 1, except that the reaction was conducted in water rather than in DMF. N-([1,1'-Biphenyl]-2-yl)acetamide was obtained as a colourless solid (43% of theory).

Example 2e

N-([1,1'-Biphenyl]-2-yl)acetamide

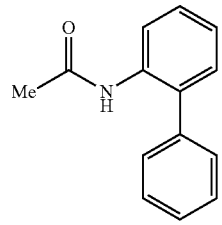 [SMILES: CC(=O)Nc1ccccc1-c1ccccc1]

The procedure was as described in Example 1, except that the reaction was conducted in DMA rather than in DMF. N-([1,1'-Biphenyl]-2-yl)acetamide was obtained as a colourless solid (46% of theory).

Example 2f

N-([1,1'-Biphenyl]-2-yl)acetamide

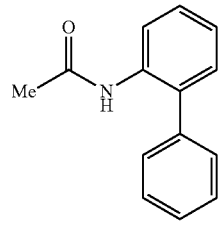 [SMILES: CC(=O)Nc1ccccc1-c1ccccc1]

The procedure was as described in Example 1, except that the reaction was conducted in DME rather than in DMF. N-([1,1'-Biphenyl]-2-yl)acetamide was obtained as a colourless solid (50% of theory).

Example 22

N-([1,1'-Biphenyl]-2-yl)acetamide

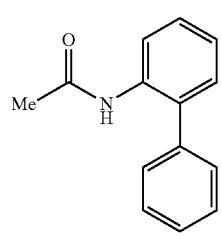 [SMILES: CC(=O)Nc1ccccc1-c1ccccc1]

The procedure was as described in Example 1, except that the reaction was conducted in a 1:1 mixture of DMF and THF rather than in DMF. N-([1,1'-Biphenyl]-2-yl)acetamide was obtained as a colourless solid (65% of theory).

Example 3a

N-([1,1'-Biphenyl]-2-yl)acetamide

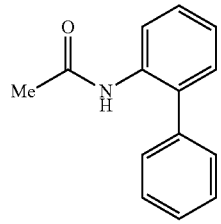 [SMILES: CC(=O)Nc1ccccc1-c1ccccc1]

In a baked-out closable reaction vessel, a suspension consisting of
acetanilide (135 mg, 1.0 mmol), [{RuCl$_2$(p-cymene)}2] (30.6 mg, 5.0 mol %), AgSbF$_6$ (68.7 mg, 0.2 mmol), Ag$_2$O (232 mg, 1.0 mmol), Fe(OTf)$_3$ (101 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 171 mg of N-([1,1'-biphenyl]-2-yl)acetamide were obtained as a colourless solid (81% of theory).

Example 3b

N-([1,1'-Biphenyl]-2-yl)acetamide

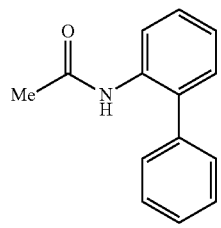 [SMILES: CC(=O)Nc1ccccc1-c1ccccc1]

The procedure was as described in Example 3a, except that the reaction was conducted in THF rather than in DMF. N-([1,1'-Biphenyl]-2-yl)acetamide was obtained in a yield of 56% of theory.

Example 4

N-([1,1'-Biphenyl]-2-yl)acetamide

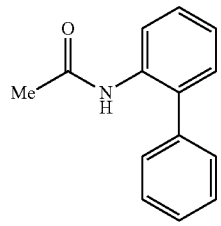 [SMILES: CC(=O)Nc1ccccc1-c1ccccc1]

In a baked-out closable reaction vessel, a suspension consisting of acetanilide (135 mg, 1.0 mmol), [{RuCl₂(p-cymene)}₂] (30.6 mg, 5.0 mol %), AgSbF₆ (68.7 mg, 0.2 mmol), Ag₂O (232 mg, 1.0 mmol), Cu(OTf)₂ (72.3 mg, 0.2 mmol) and diphenylborinic acid (137 mg, 0.75 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 84.4 mg of N-([1,1'-biphenyl]-2-yl)acetamide were obtained as a colourless solid (40% of theory).

Example 5

N-(4-Methyl-[1,1'-biphenyl]-2-yl)acetamide

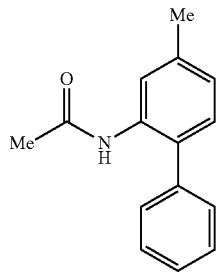 [SMILES: CC(=O)Nc1cc(C)ccc1-c1ccccc1]

In a baked-out closable reaction vessel, a suspension consisting of N-(m-tolyl)acetamide (149 mg, 1.0 mmol), [{RuCl₂(p-cymene)}₂] (30.6 mg, 5.0 mol %), AgSbF₆ (68.7 mg, 0.2 mmol), Ag₂O (232 mg, 1.0 mmol), Cu(OTf)₂ (72.3 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 175 mg of N-(4-methyl-[1,1'-biphenyl]-2-yl)acetamide were obtained as a colourless solid (78% of theory). M.p.=139-141° C. $^1$H NMR (CDCl₃, 300 MHz): δ=8.04 (s, 1H), 7.50-7.28 (m, 5H), 7.21-7.08 (m, 2H), 6.98 (d, J=7.6 Hz, 1H), 2.38 (s, 3H), 1.98 (s, 3H). $^{13}$C NMR (CDCl₃, 125 MHz): δ=168.0 ($C_q$), 138.3 ($C_q$), 138.1 ($C_q$), 134.3 ($C_q$), 129.7 (CH), 129.4 ($C_q$), 129.2 (CH), 128.9 (CH), 127.6 (CH), 125.1 (CH), 122.2 (CH), 24.6 (CH₃), 21.5 (CH₃). IR (neat): 3224, 3029, 2916, 1652, 1539, 1476, 1412, 1297, 820, 763, 724, 700, 611, 524 cm$^{-1}$. MS (EI) m/z (relative intensity): 225 ([M⁺] 54), 183 (100), 167 (30), 43 (20). HR-MS (ESI) m/z calculated for C₁₅H₁₅NO [M+] 225.1154. found 225.1159.

Example 6

N-(5-Methyl-[1,1'-biphenyl]-2-yl)acetamide

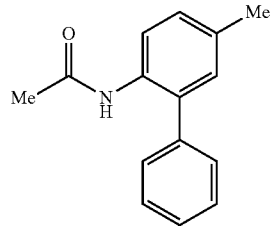 [SMILES: CC(=O)Nc1ccc(C)cc1-c1ccccc1]

In a baked-out closable reaction vessel, a suspension consisting of

N-(p-tolyl)acetamide (149 mg, 1.0 mmol), [{RuCl₂(p-cymene)}₂] (30.6 mg, 5.0 mol %), AgSbF₆ (68.7 mg, 0.2 mmol), Ag₂O (232 mg, 1.0 mmol), Cu(OTf)₂ (72.3 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 178 mg of N-(5-methyl-[1,1'-biphenyl]-2-yl)acetamide were obtained as a colourless solid (79% of theory). M.p.=107-109° C. $^1$H NMR (CDCl₃, 300 MHz): δ=8.06 (d, J=8.3 Hz, 1H), 7.50-7.31 (m, 5H), 7.16 (dd, J=8.3, 2.2 Hz, 1H), 7.04 (m, 2H), 2.33 (s, 3H), 1.99 (s, 3H). $^{13}$C NMR (CDCl₃, 126 MHz): δ=168.0 ($C_q$), 138.3 ($C_q$), 134.0 ($C_q$), 132.3 ($C_q$), 132.0 ($C_q$), 131.0 (CH), 129.1 (CH), 128.9 (CH), 128.8 (CH), 127.7 (CH), 121.9 (CH), 24.5 (CH₃), 20.9 (CH₃). IR (neat): 3235, 3057, 3029, 2922, 1655, 1524, 1505, 1488, 1366, 761, 734, 691, 603, 580 cm$^{-1}$. MS (EI) m/z (relative intensity): 225 ([M⁺] 54), 183 (100), 167 (18), 43 (22). HR-MS (ESI) m/z calculated for C₁₅H₁₅NO [M+] 225.1154. found 225.1154.

Example 7

N-(3',4'-Dichloro-5-fluoro-[1,1'-biphenyl]-2-yl)acetamide

In a baked-out closable reaction vessel, a suspension consisting of

N-(4-fluorophenyl)acetamide (153 mg, 1.0 mmol), [{RuCl₂(p-cymene)}₂] (30.6 mg, 5.0 mol %), AgSbF₆ (68.7 mg, 0.2 mmol), Ag₂O (232 mg, 1.0 mmol), Cu(OTf)₂ (72.3 mg, 0.2 mmol) and 3,4-dichlorophenylboronic acid (286 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 188 mg of N-(3',4'-dichloro-5-fluoro-[1,1'-biphenyl]-2-yl)acetamide were obtained as a colourless solid (63% of theory). M.p.=146-148° C. $^1$H NMR (CDCl$_3$, 300 MHz): δ=8.02-7.94 (m, 1H), 7.53 (d, J=8.2 Hz, 1H), 7.44 (d, J=2.0 Hz, 1H), 7.18 (dd, J=8.2, 2.1 Hz, 1H), 7.12-7.01 (m, 1H), 6.96-6.93 (m, 2H), 2.02 (s, 3H). $^{13}$C NMR (CDCl$_3$, 75 MHz): δ=168.5 (C$_q$), 159.5 (C$_q$, J$_{C-F}$=246.4 Hz), 137.2 (C$_q$, J$_{C-F}$=1.6 Hz), 133.3 (C$_q$), 133.0 (C$_q$, J$_{C-F}$=7.6 Hz), 132.8 (C$_q$), 131.0 (CH), 130.9 (CH), 130.4 (C$_q$, J$_{C-F}$=2.7 Hz), 128.2 (CH), 125.4 (CH, J$_{C-F}$=8.0 Hz), 116.5 (CH, J$_{C-F}$=23.2 Hz), 115.7 (CH, J$_{C-F}$=21.9 Hz), 24.2 (CH$_3$). $^{19}$F NMR (282 MHz, CDCl$_3$) δ=-116.6 (s). IR (neat): 3242, 3190, 1652, 1529, 1472, 1371, 1183, 863, 823, 702, 685, 607, 501 cm$^{-1}$. MS (EI) m/z (relative intensity): 297 ([M$^+$] 48), 255 (100), 219 (40), 185 (52), 157 (17), 43 (60). HR-MS (ESI) m/z calculated for C$_{14}$H$_{10}$Cl$_2$FNO [M$^+$] 297.0123. found 297.0128.

Example 8

N-([1,1'-Biphenyl]-2-yl)acetamide

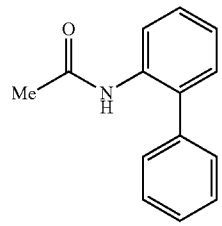 [SMILES: CC(=O)Nc1ccccc1-c1ccccc1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Na(OTf) (34.4 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. According to NMR analysis, the crude product thus obtained contained 65% of theory of N-([1,1'-biphenyl]-2-yl)acetamide.

Example 9

N-([1,1'-Biphenyl]-2-yl)acetamide

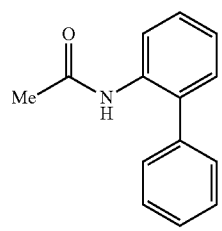 [SMILES: CC(=O)Nc1ccccc1-c1ccccc1]

The procedure was as described in Example 8, except that the reaction was conducted in the presence of 0.2 mmol of Zn(OTf)$_2$ rather than NaOTf. N-([1,1'-Biphenyl]-2-yl)acetamide was obtained in a yield of 74% of theory.

Example 10

N-([1,1'-Biphenyl]-2-yl)acetamide

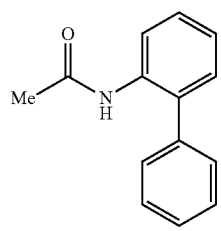 [SMILES: CC(=O)Nc1ccccc1-c1ccccc1]

The procedure was as described in Example 8, except that the reaction was conducted in the presence of 0.2 mmol of Mn(OTf)$_2$ rather than NaOTf. N-([1,1'-Biphenyl]-2-yl)acetamide was obtained in a yield of 76% of theory.

Example 11

N-([1,1'-Biphenyl]-2-yl)acetamide

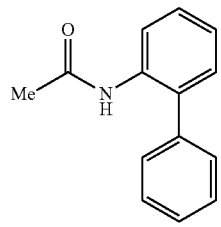 [SMILES: CC(=O)Nc1ccccc1-c1ccccc1]

The procedure was as described in Example 8, except that the reaction was conducted in the presence of 0.2 mmol of Ni(OTf)$_2$ rather than NaOTf. N-([1,1'-Biphenyl]-2-yl)acetamide was obtained in a yield of 82% of theory.

Example 12

N-([1,1'-Biphenyl]-2-yl)acetamide

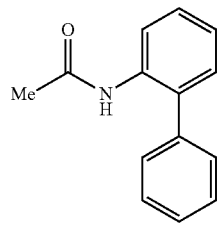 [SMILES: CC(=O)Nc1ccccc1-c1ccccc1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), CuSO$_4$ (31.9 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 91 mg of N-([1,1'-biphenyl]-2-yl)acetamide were obtained as a colourless solid (43% of theory).

Example 13

N-(3',4',5'-Trifluoro-[1,1'-biphenyl]-2-yl)acetamide

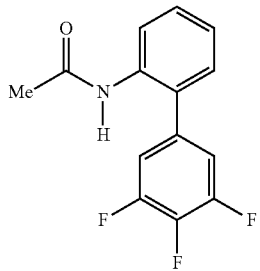 [SMILES: CC(=O)Nc1ccccc1-c1cc(F)c(F)c(F)c1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and 3,4,5-trifluorophenylboronic acid (264 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 180 mg of N-(3',4',5'-trifluoro-[1,1'-biphenyl]-2-yl)acetamide were obtained as a colourless solid (68% of theory). M.p.=140-141° C. $^1$H NMR (CDCl$_3$, 300 MHz): δ=8.08 (d, J=8.1 Hz, 1H), 7.40 (ddd, J=8.5, 5.9, 3.1 Hz, 1H), 7.24-7.17 (m, 2H), 7.06-6.97 (m, 2H), 6.93 (s, 1H), 2.07 (s, 3H). $^{13}$C NMR (CDCl$_3$, 126 MHz): δ=168.1 (C$_q$), 151.39 (ddd, J$_{C-F}$=251.6, 10.0, 4.2 Hz) (C$_q$), 139.5 (dt, J$_{C-F}$=253.1, 15.0 Hz) (C$_q$), 134.5 (C$_q$), 134.5 (C$_q$), 130.5 (C$_q$), 129.8 (CH), 129.5 (CH), 125.1 (CH), 123.3 (CH), 113.5 (dd, J$_{C-F}$=16.1, 5.4 Hz) (CH), 24.3 (CH$_3$). $^{19}$F NMR (282 MHz, CDCl$_3$) δ=−132-8-133.0 (m), −161.0 (tt, J$_{C-F}$=20.6, 6.5 Hz). IR (neat): 3263, 3040, 2934, 2864, 1660, 1526, 1483, 1417, 1359, 1278, 1241, 1036, 872, 857, 762, 695, 669, 634, 606, 547, 465 cm$^{-1}$. MS (EI) m/z (relative intensity): 265 ([M$^+$] 29), 223 (100), 203 (16), 175 (5), 169 (5), 84 (6), 43 (41). HR-MS (ESI) m/z calculated for C$_{14}$H$_{10}$F$_3$NO [M$^+$] 265.0714. found 265.0718.

Example 14

N-(4'-Chloro-[1,1'-biphenyl]-2-yl)acetamide

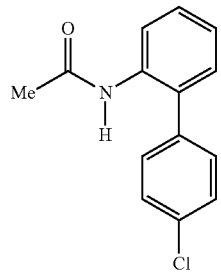 [SMILES: CC(=O)Nc1ccccc1-c1ccc(Cl)cc1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and 4-chlorophenylboronic acid (234 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 172 mg of N-(4'-chloro-[1,1'-biphenyl]-2-yl)acetamide were obtained as a colourless solid (70% of theory).
M.p.=114-116° C. $^1$H NMR (CDCl$_3$, 300 MHz): δ=8.16 (d, J=8.2 Hz, 1H), 7.46-7.40 (m, 2H), 7.39-7.32 (m, 1H), 7.31-7.26 (m, 2H), 7.20-7.17 (m, 2H), 7.01 (s, 1H), 2.01 (s, 3H). $^{13}$C NMR (CDCl$_3$, 126 MHz): δ=168.1 (C$_q$), 136.5 (C$_q$), 134.4 (C$_q$), 134.0 (C$_q$), 131.3 (C$_q$), 130.5 (CH), 129.9 (CH), 129.1 (CH), 128.6 (CH), 124.6 (CH), 122.2 (CH), 24.6 (CH$_3$). IR (neat): 3247, 3031, 2924, 2854, 1635, 1527, 1369, 1283, 1086, 828, 756, 607, 530, 489 cm$^{-1}$. MS (EI) m/z (relative intensity): 245 ([M$^+$] 35), 203 (100), 167 (43), 139 (12), 84 (17), 43 (36). HR-MS (ESI) m/z calculated for C$_{14}$H$_{12}$ClNO [M$^+$] 245.0607. found 245.0599.

Example 15

N-(5-Methoxy-[1,1'-biphenyl]-2-yl)acetamide

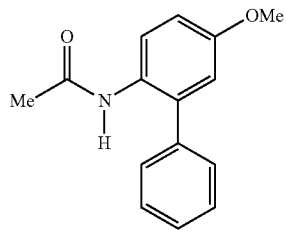 [SMILES: COc1ccc(NC(C)=O)c(-c2ccccc2)c1]

In a baked-out closable reaction vessel, a suspension consisting of
4-methoxyacetanilide (165 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and 4-chlorophenylboronic acid (234 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 183 mg of N-(5-methoxy-[1,1'-biphenyl]-2-yl)acetamide were obtained as a colourless solid (76% of theory). M.p.=112-114° C. $^1$H NMR (CDCl$_3$, 300 MHz): δ=7.95 (d, J=8.9 Hz, 1H), 7.50-7.28 (m, 5H), 6.98 (s, 1H), 6.88 (dd, J=8.9, 3.0 Hz, 1H), 6.78 (d, J=3.0 Hz, 1H), 3.78 (s, 3H), 1.97 (s, 3H). $^{13}$C NMR (CDCl$_3$, 126 MHz): δ=168.2 (C$_q$), 156.3 (C$_q$), 138.1 (C$_q$), 134.7 (C$_q$), 128.9 (CH), 128.8 (CH), 127.8 (CH), 127.6 (C$_q$), 124.3 (CH), 115.3 (CH), 113.3 (CH), 55.5 (CH$_3$), 24.2 (CH$_3$).

IR (neat): 3263, 3058, 2969, 2939, 2838, 1664, 1480, 1270, 1207, 1178, 1033, 701, 599, 512 cm$^{-1}$. MS (EI) m/z (relative intensity): 241 ([M$^+$] 71), 199 (76), 184 (100), 154 (21), 128 (11), 43 (34). HR-MS (ESI) m/z calculated for C$_{15}$H$_{15}$NO$_2$ [M$^+$] 241.1103. found 241.1106.

Example 16

N-(4-Methoxy-[1,1'-biphenyl]-2-yl)acetamide

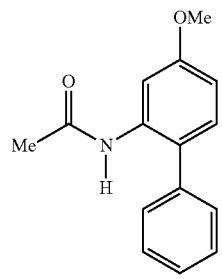 [SMILES: COc1ccc(-c2ccccc2)c(NC(C)=O)c1]

In a baked-out closable reaction vessel, a suspension consisting of 3-methoxyacetanilide (165 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and 4-chlorophenylboronic acid (234 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 174 mg of N-(4-methoxy-[1,1'-biphenyl]-2-yl)acetamide were obtained as a colourless solid (72% of theory). M.p.=91-93° C. $^1$H NMR (CDCl$_3$, 300 MHz): δ=7.98 (d, J=2.6 Hz, 1H), 7.49-7.42 (m, 2H), 7.40-7.36 (m, 1H), 7.35-7.32 (m, 1H), 7.32-7.29 (m, 1H), 7.17 (s, 1H), 7.12 (d, J=8.5 Hz, 1H), 6.72 (dd, J=8.5, 2.6 Hz, 1H), 3.84 (s, 3H), 2.00 (s, 3H). $^{13}$C NMR (CDCl$_3$, 126 MHz): δ=168.1 (C$_q$), 159.4 (C$_q$), 137.9 (C$_q$), 135.6 (C$_q$), 130.6 (CH), 129.3 (CH), 129.0 (CH), 127.6 (CH), 124.2 (C$_q$), 110.5 (CH), 106.2 (CH), 55.5 (CH$_3$), 24.8 (CH$_3$). IR (neat): 3415, 3241, 3033, 2953, 2831, 1652, 1309, 1233, 762, 724, 698, 621, 525 cm$^{-1}$. MS (EI) m/z (relative intensity): 241 ([M$^+$] 74), 199 (100), 170 (16), 156 (19), 84 (9), 43 (34). HR-MS (ESI) m/z calculated for C$_{15}$H$_{15}$NO$_2$ [M$^+$] 241.1103. found 241.1107.

Example 17

N-(5-Ethyl-[1,1'-biphenyl]-2-yl)acetamide

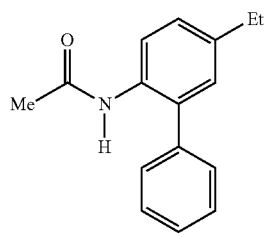 [SMILES: CCc1ccc(NC(C)=O)c(-c2ccccc2)c1]

In a baked-out closable reaction vessel, a suspension consisting of 4-ethylacetanilide (163 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 151 mg of N-(5-ethyl-[1,1'-biphenyl]-2-yl)acetamide were obtained as a colourless solid (63% of theory). M.p.=64-65° C. $^1$H NMR (CDCl$_3$, 300 MHz): δ=8.07 (d, J=8.3 Hz, 1H), 7.54-7.31 (m, 5H), 7.20 (dd, J=8.3, 2.3 Hz, 1H), 7.13 (s, 1H), 7.09 (d, J=2.3 Hz, 1H), 2.65 (q, J=7.6 Hz, 2H), 2.00 (s, 3H), 1.25 (t, J=7.6 Hz, 3H). $^{13}$C NMR (CDCl$_3$, 126 MHz): δ=168.0 (C$_q$), 140.3 (C$_q$), 138.3 (C$_q$), 132.5 (C$_q$), 132.1 (C$_q$), 129.3 (CH), 129.0 (CH), 128.8 (CH), 127.6 (CH), 127.5 (CH), 122.2 (CH), 28.3 (CH$_2$), 24.4 (CH$_3$), 15.6 (CH$_3$). IR (neat): 3424, 3267, 3027, 2964, 2930, 2871, 1659, 1513, 1487, 1410, 1368, 1297, 767, 699, 509 cm$^{-1}$. MS (EI) m/z (relative intensity): 239 ([M$^+$] 58), 197 (58), 182 (100), 180 (19), 167 (16), 43 (37). HR-MS (ESI) m/z calculated for C$_{16}$H$_{17}$NO [M$^+$] 239.1310. found 239.1306.

Example 18

N-(5-Hydroxy-[1,1'-biphenyl]-2-yl)acetamide

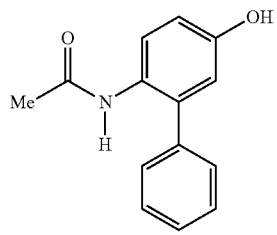 [SMILES: CC(=O)Nc1ccc(O)cc1-c1ccccc1]

In a baked-out closable reaction vessel, a suspension consisting of 4-hydroxyacetanilide (151 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 157 mg of N-(5-hydroxy-[1,1'-biphenyl]-2-yl)acetamide were obtained as a colourless solid (69% of theory). $^1$H NMR (CDCl$_3$, 300 MHz): δ=7.59 (d, J=9.5 Hz, 1H), 7.53 (s, 1H), 7.43-7.32 (m, 3H), 7.30-7.24 (m, 2H), 7.05 (s, 1H), 6.73-6.67 (m, 2H), 1.99 (s, 3H). $^{13}$C NMR (CDCl$_3$, 126 MHz): δ=169.7 ($C_q$), 154.1 ($C_q$), 138.1 ($C_q$), 136.1 ($C_q$), 128.8 (CH), 128.6 (CH), 127.6 (CH), 126.0 ($C_q$), 125.7 (CH), 117.1 (CH), 115.3 (CH), 23.9 (CH$_3$). IR (neat): 3268, 3057, 2959, 2926, 2795, 1524, 1488, 1433, 1299, 1199, 726, 699, 646, 506 cm$^{-1}$. MS (EI) m/z (relative intensity): 227 ([M$^+$] 44), 185 (100), 154 (11), 43 (14). HR-MS (ESI) m/z calculated for C$_{14}$H$_{13}$NO$_2$ [M$^+$] 227.0946. found 227.0945.

Example 19

N-(4'-Methyl-[1,1'-biphenyl]-2-yl)acetamide

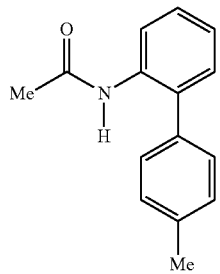 [SMILES: CC(=O)Nc1ccccc1-c1ccc(C)cc1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and 4-methylphenylboronic acid (204 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 185 mg of N-(4'-methyl-[1,1'-biphenyl]-2-yl)acetamide were obtained as a colourless solid (82% of theory). M.p.=106-108° C. $^1$H NMR (CDCl$_3$, 300 MHz): δ=8.24 (d, J=8.2 Hz, 1H), 7.44-7.06 (m, 8H), 2.41 (s, 3H), 2.01 (s, 3H). $^{13}$C NMR (CDCl$_3$, 126 MHz): δ=168.0 ($C_q$), 137.6 ($C_q$), 135.0 ($C_q$), 134.6 ($C_q$), 132.0 ($C_q$), 130.0 (CH), 129.7 (CH), 128.9 (CH), 128.1 (CH), 124.1 (CH), 121.4 (CH), 24.6 (CH$_3$), 21.2 (CH$_3$). IR (neat): 3340, 2956, 2921, 2853, 1515, 1442, 1282, 817, 756, 680, 598, 522, 488 cm$^{-1}$. MS (EI) m/z (relative intensity): 225 ([M$^+$] 55), 183 (100), 167 (37), 43 (26). HR-MS (ESI) m/z calculated for C$_{15}$H$_{15}$NO [M$^+$] 225.1154. found 225.1149.

Example 20

N-(4'-Methoxy-[1,1'-biphenyl]-2-yl)acetamide

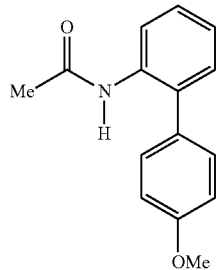 [SMILES: COc1ccc(-c2ccccc2NC(C)=O)cc1]

In a baked-out closable reaction vessel, a suspension consisting of
acetanilide (135 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and 4-methoxyphenylboronic acid (228 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 200 mg of N-(4'-methyl-[1,1'-biphenyl]-2-yl)acetamide were obtained as a colourless solid (83% of theory). M.p.=135-137° C. $^1$H NMR (CDCl$_3$, 300 MHz): δ=8.20 (d, J=8.2 Hz, 1H), 7.34-7.24 (m, 3H), 7.23-7.09 (m, 3H), 6.98 (d, J=8.6 Hz, 2H), 3.84 (s, 3H), 2.00 (s, 3H). $^{13}$C NMR (CDCl$_3$, 126 MHz): δ=168.3 ($C_q$), 159.3 ($C_q$), 134.8 ($C_q$), 132.0 ($C_q$), 130.3 (CH), 130.2 ($C_q$), 130.1 (CH), 128.0 (CH), 124.3 (CH), 121.6 (CH), 114.4 (CH), 55.2 (CH$_3$), 24.4 (CH$_3$). IR (neat): 3351, 3012, 2921, 2842, 1690, 1602, 1512, 1439, 1362, 1294, 1239, 1175, 1031, 832, 800, 770, 663, 581, 560, 534 cm$^{-1}$. MS (EI) m/z (relative intensity): 241 ([M$^+$] 54), 199 (100), 184 (37), 154 (24), 128 (12), 43 (30). HR-MS (ESI) m/z calculated for C$_{15}$H$_{15}$NO$_2$ [M$^+$] 241.1103. found 241.1110.

Example 21

N-(Biphenyl-2-yl)-2-methylpropanamide

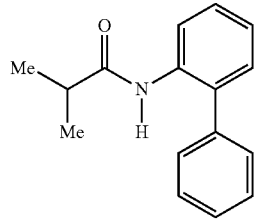 [SMILES: CC(C)C(=O)Nc1ccccc1-c1ccccc1]

In a baked-out closable reaction vessel, a suspension consisting of
2-methyl-N-phenylpropanamide (163 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 131 mg of N-(biphenyl-2-yl)-2-methylpropanamide were obtained as a colourless solid (55% of theory). M.p.=126-128° C. $^1$H NMR (CDCl$_3$, 300 MHz): δ=8.33 (d, J=8.2 Hz, 1H), 7.54-7.33 (m, 6H), 7.28-7.13 (m, 3H), 2.4 (hept, J=6.8 Hz, 1H), 1.2 (d, J=6.8 Hz, 6H). $^{13}$C NMR (CDCl$_3$, 126 MHz): δ=174.8 (C$_q$), 138.1 (C$_q$), 134.9 (C$_q$), 132.1 (C$_q$), 129.9 (CH), 129.3 (CH), 129.0 (CH), 128.4 (CH), 128.0 (CH), 124.0 (CH), 121.3 (CH), 36.7 (CH), 19.3 (CH$_3$). IR (neat): 3218, 2964, 1649, 1520, 1480, 1239, 1203, 1099, 776, 748, 726, 702, 542 cm$^{-1}$. MS (EI) m/z (relative intensity): 239 ([M$^+$] 29), 169 (100), 71(6), 43 (30). HR-MS (ESI) m/z calculated for C$_{16}$H$_{17}$NO [M$^+$] 239.1310. found 239.1314.

Example 22

N-(Biphenyl-2-yl)-2,2-dimethylpropanamide

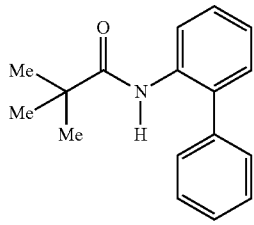 [SMILES: CC(C)(C)C(=O)Nc1ccccc1-c1ccccc1]

In a baked-out closable reaction vessel, a suspension consisting of
2,2-dimethyl-N-phenylpropanamide (177 mg, 1.0 mmol), [{RuCl$_2$(p-cymene)}$_2$] (30.6 mg, 5.0 mol %), AgSbF$_6$ (68.7 mg, 0.2 mmol), Ag$_2$O (232 mg, 1.0 mmol), Cu(OTf)$_2$ (72.3 mg, 0.2 mmol) and phenylboronic acid (183 mg, 1.5 mmol) in dry DMF (3.0 ml) was stirred in a nitrogen atmosphere at 110° C. for 20 h. The reaction mixture was then diluted at room temperature with EtOAc (75 ml) and filtered through Celite and silica gel, and the filtrate was concentrated. The crude product thus obtained was purified by chromatography on silica gel (n-hexane/EtOAc: 7/3). 114 mg of N-(biphenyl-2-yl)-2,2-dimethylpropanamide were obtained as a colourless solid (45% of theory). M.p.=68-69° C. $^1$H NMR (CDCl$_3$, 300 MHz): δ=8.37 (dd, J=8.2, 1.2 Hz, 1H), 7.54-7.33 (m, 7H), 7.24 (dd, J=7.4, 1.7 Hz, 1H), 7.17 (dd, J=7.4, 1.7 Hz, 1H), 1.09 (s, 9H). $^{13}$C NMR (CDCl$_3$, 126 MHz): δ=176.1 (C$_q$), 138.0 (C$_q$), 135.0 (C$_q$), 132.0 (C$_q$), 129.6 (CH), 129.2 (CH), 128.9 (CH), 128.4 (CH), 127.9 (CH), 123.8 (CH), 120.8 (CH), 39.8 (C$_q$), 27.4 (CH$_3$). IR (neat): 3259, 3056, 2970, 2904, 2868, 1646, 1503, 1477, 771, 743, 700, 647 cm$^{-1}$. MS (EI) m/z (relative intensity): 253 ([M$^+$] 53), 169 (60), 57 (100), 41 (17). HR-MS (ESI) m/z calculated for C$_{17}$H$_{19}$NO [M$^+$] 253.1467. found 253.1472.

The invention claimed is:
1. A process for the preparation of one or more biphenyl-amides of formula (V)

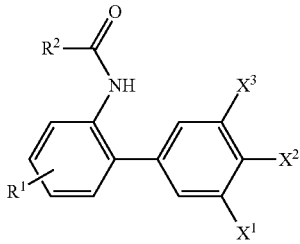

wherein
R$^1$ is hydrogen, hydroxyl, fluorine, chlorine, C$_1$-C$_4$-alkyl, C$_1$-C$_4$-alkoxy, C$_1$-C$_4$-alkylthio or C$_1$-C$_4$-haloalkyl,
R$^2$ is C$_1$-C$_4$-alkyl, C$_6$-C$_{10}$-aryl or C$_6$-C$_{10}$-aryl-CH$_2$—, and
X$^1$ is hydrogen, C$_1$-C$_4$-alkyl, C$_1$-C$_4$-alkoxy, fluorine or chlorine,
X$^2$ is hydrogen, C$_1$-C$_4$-alkyl, C$_1$-C$_4$-alkoxy, fluorine or chlorine,
X$^3$ is hydrogen, C$_1$-C$_4$-alkyl, C$_1$-C$_4$-alkoxy, fluorine or chlorine,
comprising reacting one or more anilides of formula (II)

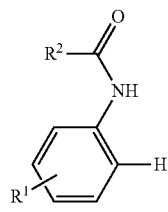

wherein
R$^1$ and R$^2$ are each as defined above,
in a solvent selected from the group consisting of N,N-dialkylalkanamides, dimethoxyethane (DME), methanol, ethyl acetate, water, and mixtures of these solvents,
with an organoboron compound of formula (III)

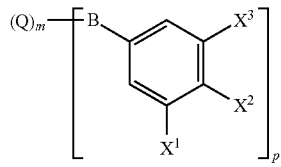

wherein
X$^1$, X$^2$ and X$^3$ are each as defined above, and which is selected from one of the following groups consisting of:
(i) boronic acids of formula (III) in which
Q is a hydroxyl group,
m is 2, and
p is 1,
or the anhydrides, dimers or trimers of these boronic acids;
(ii) boronic acid derivatives of formula (III) in which
Q is F, Cl, Br, I, C$_1$-C$_4$-alkyl, C$_6$-C$_{10}$-aryl, C$_1$-C$_4$-alkoxy or C$_6$-C$_{10}$-aryloxy,
m is 2, and
p is 1;

(iii) borinic acids of formula (III) in which
Q is OH, F, $C_1$, Br, I, $C_1$-$C_4$-alkyl, $C_6$-$C_{10}$-aryl, $C_1$-$C_4$-alkoxy or $C_6$-$C_{10}$-aryloxy,
m is 1, and
p is 2;
(iv) cyclic boronic esters of formula (III) in which
Q is a $C_2$-$C_3$-alkyldioxy radical which, together with the boron atom to which it is bonded, forms a 5- or 6-membered ring optionally substituted by one or more $C_1$-$C_4$-alkyl radicals,
m is 1, and
p is 1;
(v) boronates of formula (III) in which
Q is OH, F, $C_1$, Br, I, $C_1$-$C_4$-alkyl, $C_6$-$C_{10}$-aryl, $C_1$-$C_4$-alkoxy or $C_6$-$C_{10}$-aryloxy,
m is 3, and
p is 1
and the negative charge of the boronate anion is compensated for by a cation,
(vi) triarylboranes of formula (III) in which
m is 0, and
p is 3; and
(vii) tetraarylborates of formula (III) in which
m is 0, and
p is 4
and the negative charge of the tetraarylborate anion is compensated for by a cation,
in the presence of a catalyst system consisting of a ruthenium catalyst, an activator, an oxidizing agent and a metal triflate.

2. A process according to claim 1, wherein an amide of formula (V) is deprotected in a second stage to give a free amine of formula (I)

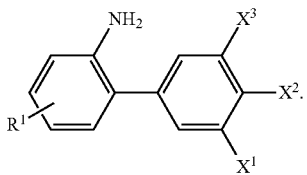

(I)

3. A process according to claim 1, wherein the solvent is selected from the group consisting of N,N-dialkylalkanamides and mixtures of these thereof.

4. A process according to claim 1, wherein the catalyst is [{RuCl$_2$(p-cymene)}$_2$].

5. A process according to claim 1, wherein the oxidizing agent is Ag$_2$O.

6. A process according to claim 1, wherein the metal of the metal triflate is selected from the group consisting of Li, Na, K, Mg, Ca, Mn, Fe, Co, Ni, Cu and Zn.

7. A process according to claim 1, wherein the metal of the metal triflate is selected from the group consisting of sodium, potassium, manganese, zinc, iron and nickel.

8. A process according to claim 1, wherein the activator is selected from the group consisting of AgSbF$_6$, KPF$_6$, NaPF$_6$, AgF and AgBF$_4$.

9. A process according to claim 1, wherein the organoboron compound of formula (III) is a boronic acid of formula (III), group (i), wherein Q=OH, m=2 and p=1.

10. A process according to claim 1, wherein the organoboron compound of formula (III) is a boronic acid of formula (III), group (i), wherein Q=OH, m=2 and p=1, the solvent is DMF, the catalyst is [{RuCl$_2$(p-cymene)}$_2$], the metal triflate is iron(III) triflate, the oxidizing agent is Ag$_2$O and the activator is AgSbF$_6$.

11. A process according to claim 1, wherein the organoboron compound of formula (III) is a boronic acid of formula (III), group (i), in which
Q is a hydroxyl group,
m is 2, and
p is 1,
or an anhydride, dimer or trimer thereof.

12. A process according to claim 1, wherein the organoboron compound of formula (III) is a boronic acid derivative of formula (III), group (ii), in which
Q is F, $C_1$, Br, I, $C_1$-$C_4$-alkyl, $C_6$-$C_{10}$-aryl, $C_1$-$C_4$-alkoxy or $C_6$-$C_{10}$-aryloxy,
m is 2, and
p is 1.

13. A process according to claim 1, wherein the organoboron compound of formula (III) is a borinic acid of formula (III), group (iii), in which
Q is OH, F, $C_1$, Br, I, $C_1$-$C_4$-alkyl, $C_6$-$C_{10}$-aryl, $C_1$-$C_4$-alkoxy or $C_6$-$C_{10}$-aryloxy,
m is 1, and
p is 2.

14. A process according to claim 1, wherein the organoboron compound of formula (III) is a cyclic boronic ester of formula (III), group (iv), in which
Q is a $C_2$-$C_3$-alkyldioxy radical which, together with the boron atom to which it is bonded, forms a 5- or 6-membered ring optionally substituted by one or more $C_1$-$C_4$-alkyl radicals,
m is 1, and
p is 1.

15. A process according to claim 1, wherein the organoboron compound of formula (III) is a boronate of formula (III), group (v), in which
Q is OH, F, Cl, Br, I, $C_1$-$C_4$-alkyl, $C_6$-$C_{10}$-aryl, $C_1$-$C_4$-alkoxy or $C_6$-$C_{10}$-aryloxy,
m is 3, and
p is 1,
and the negative charge of the boronate anion is compensated for by a cation.

16. A process according to claim 1, wherein the organoboron compound of formula (III) is a triarylborane of formula (III), group (vi), in which
m is 0, and
p is 3.

17. A process according to claim 1, wherein the organoboron compound of formula (III) is a tetraarylborate of formula (III), group (vii), in which
m is 0, and
p is 4,
and the negative charge of the tetraarylborate anion is compensated for by a cation.

18. A process according to claim 1, wherein the solvent is water.

19. A process according to claim 1, wherein the solvent is dimethylformamide (DMF).

20. A process according to claim 1, wherein the solvent is N-methylpyrrolidone (NMP).

* * * * *